United States Patent
Barrett

(10) Patent No.: US 7,357,779 B2
(45) Date of Patent: Apr. 15, 2008

(54) ASPIRATION FLOW MODULATION DEVICE

(76) Inventor: Graham David Barrett, 6 Dampier Avenue, City Beach, Western Australia 6015 (AU)

( * ) Notice: Subject to any disclaimer, the term of this patent is extended or adjusted under 35 U.S.C. 154(b) by 93 days.

(21) Appl. No.: 10/239,476

(22) PCT Filed: Mar. 23, 2001

(86) PCT No.: PCT/AU01/00322

§ 371 (c)(1),
(2), (4) Date: Sep. 23, 2002

(87) PCT Pub. No.: WO01/70152

PCT Pub. Date: Sep. 27, 2001

(65) Prior Publication Data

US 2003/0078591 A1    Apr. 24, 2003

(30) Foreign Application Priority Data

Mar. 23, 2000 (AU) .................... PQ6444

(51) Int. Cl.
*A61M 3/00* (2006.01)
(52) U.S. Cl. .............................. 604/43; 604/22
(58) Field of Classification Search ............. 604/43
See application file for complete search history.

(56) References Cited

U.S. PATENT DOCUMENTS

| 3,902,495 A | | 9/1975 | Weiss |
|---|---|---|---|
| 4,832,685 A | | 5/1989 | Haines |
| 4,921,477 A | | 5/1990 | Davies |
| 5,185,002 A | | 2/1993 | Venturini |
| 5,248,297 A | * | 9/1993 | Takase ................ 604/22 |
| 5,470,312 A | | 11/1995 | Zanger et al. |
| 5,718,676 A | * | 2/1998 | Barrett ................ 604/22 |
| 6,183,433 B1 | * | 2/2001 | Bays ................ 604/22 |

FOREIGN PATENT DOCUMENTS

| AU | 684224 | | 12/1997 |
|---|---|---|---|
| AU | 717553 | | 3/1998 |
| WO | 98/07398 | | 2/1998 |
| WO | WO 98/07398 | * | 2/1998 |

\* cited by examiner

*Primary Examiner*—Nicholas D. Lucchesi
*Assistant Examiner*—Laura Bouchelle
(74) *Attorney, Agent, or Firm*—Pearne & Gordon LLP

(57) ABSTRACT

An aspiration flow modulation device (10, 20, 50) having an irrigation line component (14, 24, 52) and an aspiration line component (12, 22, 54). A fluid communication lumen (12, 28, 75) extends between the components so as to provide a flow of fluid to reduce pressure variations in the event that the aspiration line becomes occluded in use.

4 Claims, 3 Drawing Sheets

ASPIRATION FLOW MODULATION DEVICE

FIELD OF THE INVENTION

The present invention relates to an aspiration flow modulation device.

BACKGROUND OF THE INVENTION

The crystalline lens of the human eye transmits and focuses light and is located behind the iris attached to the wall of the eye by suspensory ligaments known as the zonules. The lens consists of a more rigid central nucleus surrounded by peripheral cortical material which has a softer consistency. A fine membrane known as the capsule contains the entire lens. The eye has an anterior chamber and a posterior chamber.

Cataract formation refers to a loss of transparency of the crystalline lens of the eye and is a common occurrence with age. This results in a progressive reduction in vision, which can be restored with surgery. Modern cataract surgery involves removal of the cataractous lens and insertion of a plastics material intraocular lens to replace the crystalline lens. Further, modem cataract surgery uses ultrasonic energy to fragment and aspirate the cataractous lens by a technique known as phacoemulsification. When the cataractous lens is removed there remains in the eye a capsular bag remnant.

A central opening in an anterior portion of the capsule allows access to lenticular material by an ultrasonic probe, which typically has an outer wall and a central lumen. A plastics material sleeve surrounding a needle provides a conduit for transmission of fluid into the eye to replace fluid aspirated from the eye in removing the lens material. Once the harder nuclear material has been removed with the assistance of ultrasonic energy the softer cortical material can be aspirated with an irrigation/aspiration cannula.

In both phases of the procedure it is important that the anterior chamber of the eye is maintained at a positive pressure and constant volume to prevent collapse. Collapse of the anterior chamber can result in trauma to sensitive ocular tissues. Contact with endothelial cells lining a posterior surface of the cornea of the eye can result in irreparable damage. Even more common is inadvertent contact or aspiration of the posterior capsule, which can result in rupture of this fine membrane. The posterior capsule prevents escape of fluid known as vitreous humour, contained in the posterior chamber of the eye. Rupture of the posterior capsule and loss of the vitreous humour increases the risk of retinal detachment and cystoid macular oedema after cataract surgery with the subsequent loss of vision. Furthermore, if the posterior capsule is disrupted during surgery it may not be feasible to place an intraocular lens in the preferred position in the capsular bag remnant of the original natural lens. This too can have a less favourable outcome than is anticipated in uncomplicated surgery.

Thus, maintenance of a stable pressure and volume in the anterior chamber is very important when performing irrigation/aspiration operations, such as phacoemulsification, on the eye. In Australian Patent Number 684224 there is described and claimed a phacoemulsification needle whilst in Australian Patent 717553 there is described and claimed an intraocular irrigation/aspiration cannula. The inventions of these patents assist the surgeon in achieving this stable pressure and volume. The present invention seeks further to reduce fluctuations in chamber pressure and volume during irrigation/aspiration of the eye.

There are two basic types of pump systems that achieve aspiration of fluid and lens material during phacoemulsification and cortical aspiration. The first are positive fluid displacement pumps such as perstaltic pumps. In this system fluid flow is generated in tubing and significant vacuum is achieved when the tubing is occluded. In the other system typified by a venturi pump vacuum is generated in a cassette and the subsequent flow and aspiration of fluid from the eye is related to a preset vacuum.

In both systems the sequence of removal of nuclear and cortical material is similar. Fluid flow is generated in the aspiration tubing and fluid is aspirated from the anterior chamber via the phacoemulsification needle or irrigation/aspiration cannula. This attracts nuclear or cortical material to the needle or cannula and occlusion of the tip or aspiration port occurs. There is then a build up of vacuum in the tubing until the negative pressure generated by the pump overcomes the resistance of the lenticular material, which is then aspirated along the tubing. At this stage there is a rapid equalisation of pressure between the anterior chamber of the eye and the rest of the system with a rapid increase in fluid flow and drop in chamber pressure. This is typically referred to as post occlusion surge and often manifests as a forward movement of the posterior capsule as the anterior chamber pressure and volume alters.

The vacuum can be reduced by foot pedal control and the machines respond by venting or equalising the pressure in the system either to fluid or to air. The venting, however, occurs some distance from the Surgeon's handpiece and the anterior chamber and there is typically a time lag before the vacuum in the tubing is restored to atmospheric or a positive pressure and the pressure in the anterior chamber of the eye is restored to the normal resting or unoccluded level. Any measures which reduce the drop in anterior chamber pressure and shortens the time to attain the resting pressure, increases the safety of the surgical procedure and reduces the likelihood of inadvertent rupture of the posterior capsule or occurrence of other problems.

SUMMARY OF THE INVENTION

In accordance with one aspect of the present invention there is provided an aspiration flow modulation device which comprises an irrigation line component and an aspiration line component wherein a fluid communication lumen is located between the irrigation line component and the aspiration line component so as to provide fluid communication between the components.

The device of the present invention allows communication between the aspiration line component, preferably close to the phacoemulsification handpiece or the irrigation/aspiration handpiece, and a positive pressure fluid infusion or irrigation line.

The positive pressure infusion line can be separate from the existing infusion line or connected to the existing infusion line. If separate the positive pressure infusion line can be fed by a separate bottle of fluid or fed from the same bottle as the main infusion line. Preferably, the fluid communication lumen is of equal or less cross sectional area than the lumen of a phacoemulsification needle or the inlet port of an irrigation aspiration cannula. Preferably, the fluid communication lumen is less than one half, more preferably less than one third, of the cross sectional area of the lumen of the phacoemulsification needle or the port of the irrigation/aspiration cannula.

When no aspiration is applied an extra infusion line allows fluid to reach the anterior chamber of the eye via the aspiration line so the resting pressure is greater. When aspiration is applied to the aspiration line, in the unoccluded state only a minimal amount of fluid is drawn through the fluid communication lumen between the aspiration line and the infusion line. In the unoccluded state, therefore, nearly all the flow is through the larger lumen of the irrigation/ aspiration device. This is important as it does not greatly reduce the efficiency of the irrigation/aspiration device in attracting fragments of lenticular material.

When occlusion of the irrigation/aspiration device occurs, the build up of vacuum is limited in the present invention by aspiration of fluid from the infusion line in a progressive fashion. The initial rise in vacuum is very similar to a system with no communication with the infusion line but the increase in vacuum is slowed as the vacuum approaches its maximum value. Thus, the vacuum limit achieved will always be slightly less than the maximum vacuum limit setting on the machine. This means that the pump may not stop as is the case with existing machines with no communication between the aspiration and infusion lines. This is also considered to be beneficial in providing efficient removal of lenticular material. Furthermore, the continued pump action results in continuous fluid flow which may help cooling of a phacoemulsification needle.

When the occlusion resistance is overcome there is an immediate flow of fluid available from the infusion line of the device of the present invention to compensate for negative pressure in the aspiration line which reduces both the magnitude and duration of the post occlusion surge. The fact that the pump action is typically continuous in the process and does not stop and then restart also provides a more stable chamber pressure and volume than that encountered with conventional systems.

The mode of operation described above is applicable both to phacoemulsification needles and to irrigation/aspiration cannulae in removal of lenticular material from the eye.

BRIEF DESCRIPTION OF THE DRAWINGS

The present invention will now be described, by way of example, with reference to the accompanying drawings, in which:

FIG. 7 is a sectional view along the line 7-7 of FIG. 4.

DETAILED DESCRIPTION OF THE PREFERRED EMBODIMENTS

Figure 1:
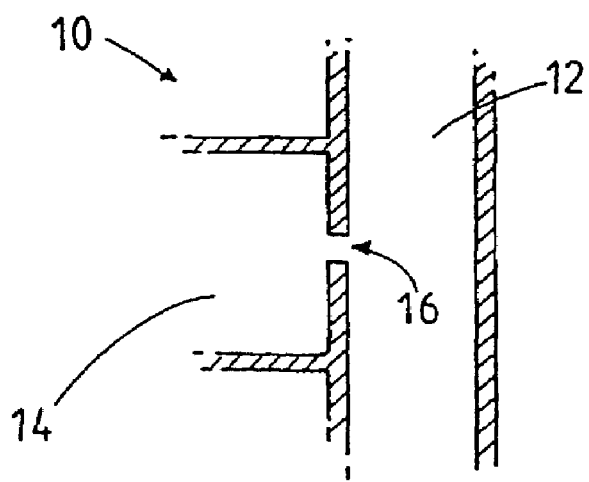
FIG. 1 is a schematic view of a device according to a first embodiment of the present invention.

In FIG. 1 of the accompanying drawings, there is shown schematically an aspiration flow modulation device 10 including an aspiration line component 12 and an irrigation or infusion line component 14 arranged in a T-shaped configuration. The irrigation line component 14 is in communication with the aspiration line component 12 by means of a narrow lumen 16. The irrigation line component 14 is preferably attached to a bottle of fluid separate to that supplying the main infusion line of the phacoemulsification device or irrigation/aspiration cannula. The aspiration line component 12 is preferably connected to the aspiration line connected to the phacoemulsification device or irrigation/ aspiration handpiece.

Figure 2:
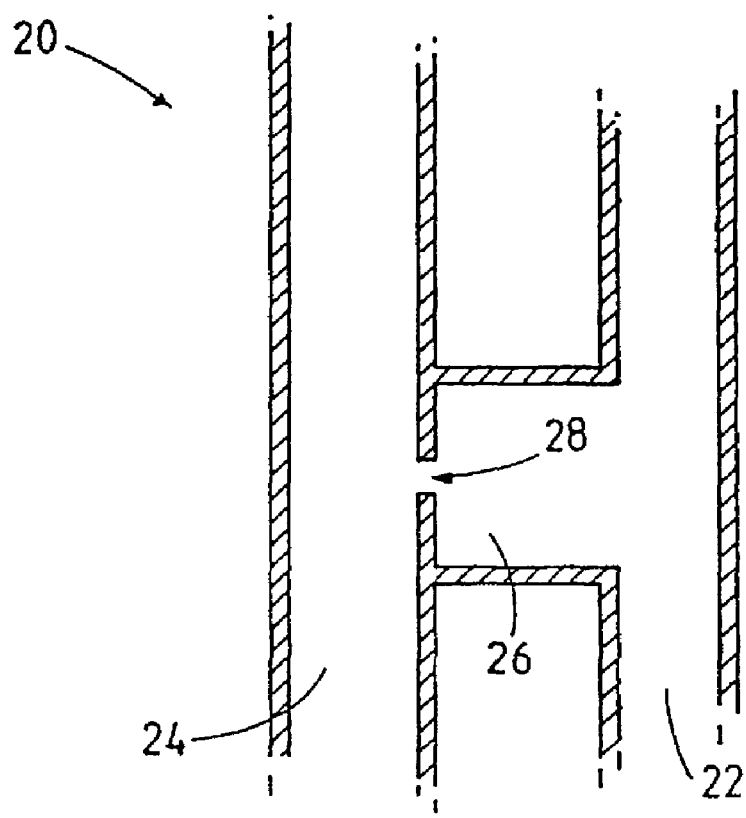
FIG. 2 is a schematic view of a device according to a second embodiment of the present invention.
Figure 3:
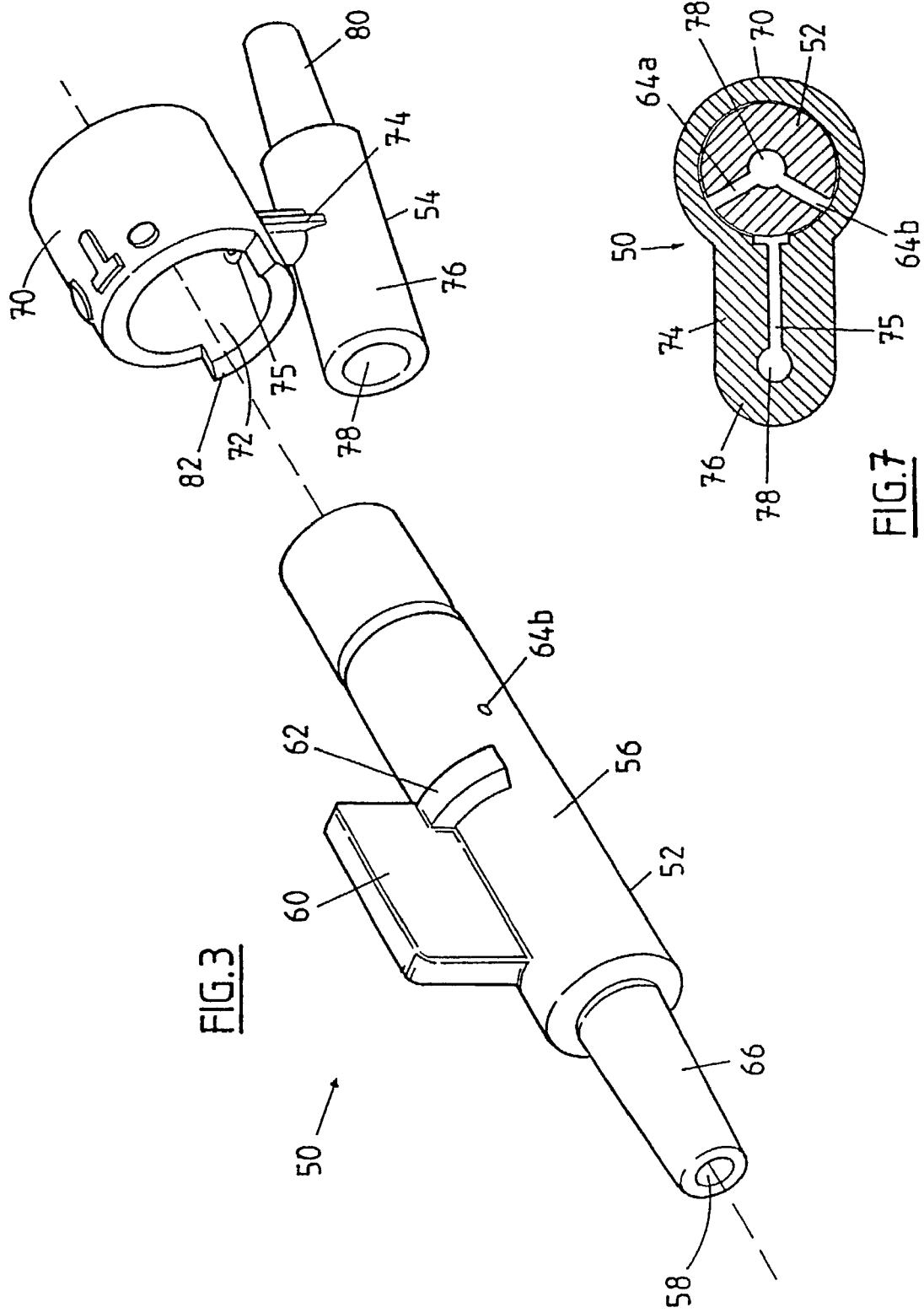
FIG. 3 of the accompanying drawings is an exploded perspective view of a preferred third embodiment of the present invention comprising two components.
Figure 4:
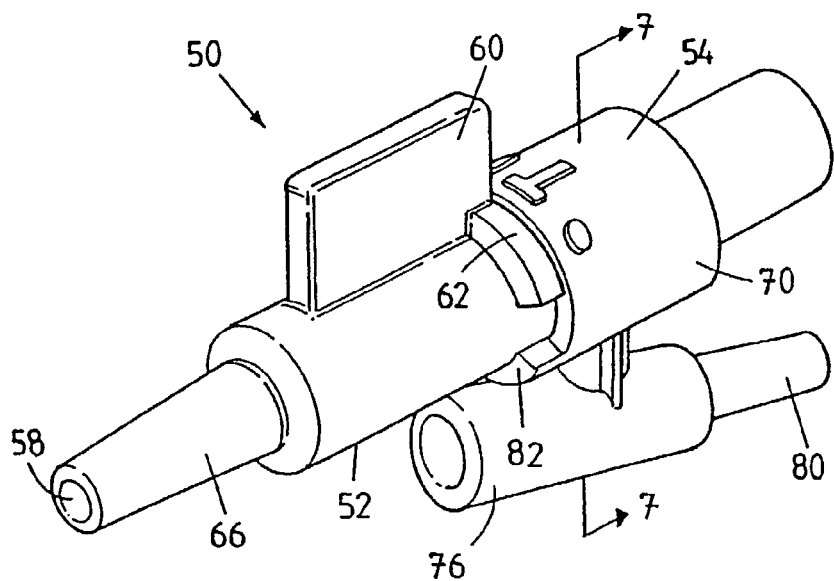
FIG. 4 is a perspective view of the embodiment of FIG. 3 in open position.
Figure 5:
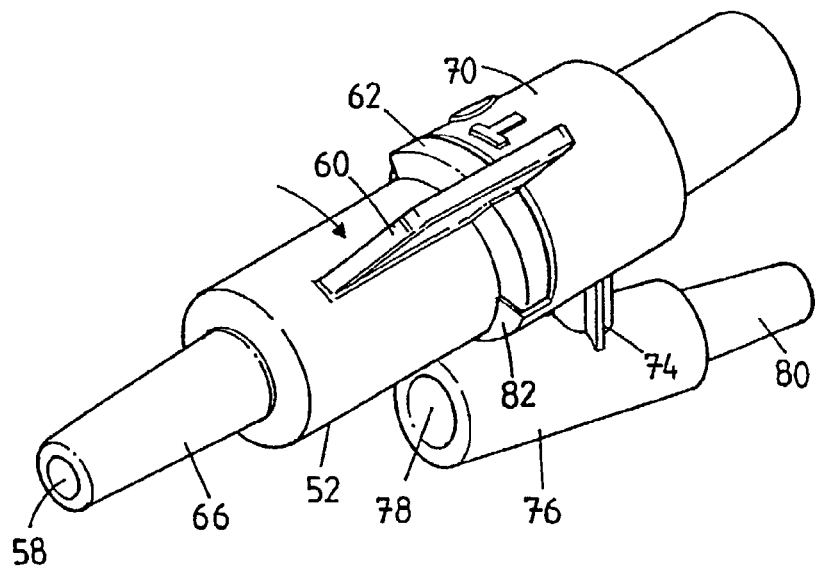
FIG. 5 is a perspective view of the embodiment of FIG. 3 in a first on position.
Figure 6:
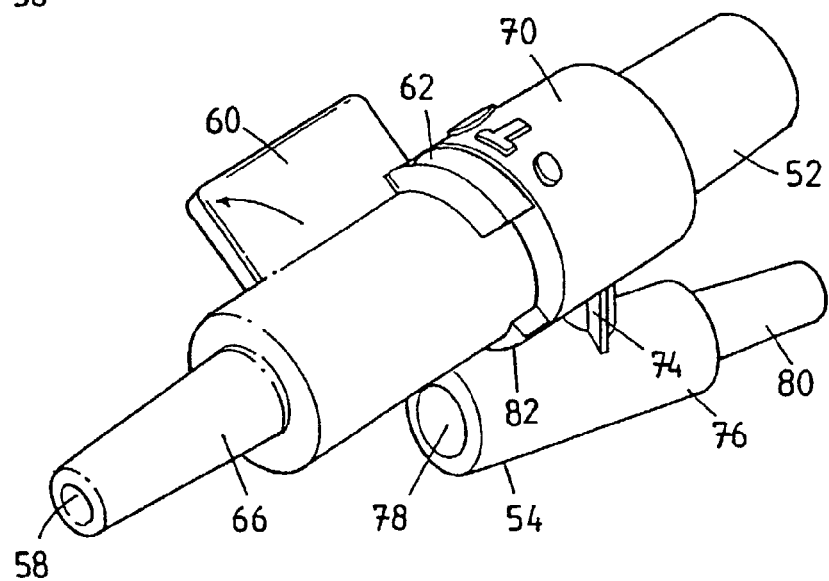
FIG. 6 is a perspective view of the embodiment of FIG. 3 in a second on position.

In FIG. 2 of the accompanying drawings, there is shown schematically an aspiration flow modulation device 20 including an aspiration line component 22 and an irrigation or infusion line component 24 arranged in an H-shaped configuration. Further, there is a transverse line 26 connecting the components 22 and 24. The transverse line 26 communicates with the irrigation line component 22 through a narrow fluid communication lumen 28.

The irrigation line component 24 is preferably connected to the infusion line supplying the phacoemulsification device or the irrigation/aspiration cannula. The aspiration line component 22 is preferably connected to the aspiration line connected to the phacoemulsification device or the irrigation/aspiration cannula.

In both configurations described above the narrow fluid communication lumen between the aspiration and irrigation line components can be fixed or variable. Predetermined lumen diameters can be switched in the pathway including a no communication option depending on individual preferences. Similarly, the lumen diameter could be varied in a continual fashion similar to a needle valve.

In FIGS. 3 to 7 of the accompanying drawings there is shown a further preferred embodiment of an aspiration flow modulation device 50 in accordance with the present invention.

The device 50 includes an infusion or irrigation line component 52 and an aspiration line component 54.

The irrigation line component 52 includes a generally cylindrical body 56 having a central bore 58 therethrough. The body 56 is also provided with an outwardly extending tab member 60 which is disposed normal to the curvature of the body 56. The body 56 also has an outwardly extending flange 62 which extends partially around the body 56 transversely of the tab member 60.

In fact, the flange 62 extends approximately about half way around the body 56.

Further, the body 56 has two small holes 64a and 64b formed therein communicating between the bore 58 and the exterior of the body 56. The holes 64a and 64b are disposed at about 120° to one another on the body 56 at the same distance from the flange 62.

The aspiration line component 54 has an annular body 70 having a bore 72 extending therethrough. Further, a bridge member 74 is provided to connect the body 70 to a tubular member 76. The tubular member 76 also has a bore 78 extending therethrough. The bridge 74 contains a longitudinally extending fluid communication lumen 75 interconnecting the bore 72 and the bore 78.

As can be seen the irrigation line component 52 has a narrow portion 66 at one end which is arranged to be attached to a hand piece, whilst the bore 58 has a widened portion at the other end to receive an infusion line.

Further, the tubular member 76 of the aspiration line component 54 has a widened portion of the bore 78 at one end which is arranged to engage with the hand piece whilst the other end of the tubular member 76 has a narrow portion 80 arranged to engage with an aspiration line.

Still further, the annular body 70 is provided with a flange 82 which extends about 120° around the annular body 70.

In operation, the components 52 and 54 are inter-engaged by inserting the component 52 into the bore 72 of the annular body 70 until the flange 62 engages with the annular body 70 and is aligned with the flange 82 thereof. The device 50 is then coupled up to a hand piece on the one side and an infusion line and an aspiration line on the other side.

The tab 60 has three positions. In a first central position, shown in FIG. 4, the holes 64a and 64b are not aligned at all with the lumen 75. In a second position of the tab 60, shown in FIG. 5, the aperture 64b is particularly aligned with the lumen 75 to permit a partial external bypass effect. In a third position of the tab 60 the aperture 64a is more fully aligned with the lumen 75 to permit a full bypass effect. The holes 64a and 64b are very small. A different degree of bypass can be obtained by the extent to which these holes align with the lumen 75 in the second and third positions discussed above. This may be achieved by configuring the entrance to the lumen 75 asymmetrically.

An alternative would be to have the holes 64a and 64b of different sizes.

In tests carried out with the invention FIGS. 3 to 7 in a phacoemulsification apparatus it has been found that the presence of the external bypass delayed the onset of collapse of a flexible chamber. The difference was noted whether the apparatus was operating in vacuum or flow priority mode. Further, in the absence of the external bypass the pump ceased operating upon occlusion of the aspiration line when the apparatus was used in flow priority mode. However, when the bypass was activated the pump continued to function during occlusion of the aspiration line.

Further, with the bypass operating the magnitude and duration of the drop in pressure during occlusion was significantly less.

The device of the present invention could be integrated in the aspiration and infusion lines supplied with a phacoemulsification machine or supplied as a separate device.

Further, instead of a device attached to the aspiration and infusion lines the fluid communication lumen could be integrated into the construction of a phacoemulsification or irrigation/aspiration cannula handpiece. It is also feasible for the communication between the aspiration and infusion lines to be integrated into the design of a removable cassette or cartridge mechanism commonly used in phacoemulsification machines. The communication between the aspiration and irrigation pathways could also be implemented in a main console of a phacoemulsification machine.

Still further, reuseable or disposable versions of the devices of the present invention are envisaged. Suitable materials for construction of the device of the present invention include metals and plastics materials. The device could be fabricated by machining or by using moulding methods of constructions.

Modifications and variations such as would be apparent to a skilled addressee are deemed within the scope of the present invention.

The invention claimed is:

1. An aspiration flow modulation device arranged to be mounted in close proximity to a hand piece wherein the device comprises an irrigation line component and an aspiration line component, and wherein the irrigation line component is arranged to be mounted in close proximity to the hand piece and the aspiration line component is also arranged to be mounted in close proximity to the hand piece, and a fluid communication lumen is located between the irrigation line component and the aspiration line component so as to provide fluid communication between the components, the device being formed in a plurality of parts, a first part having the irrigation line component and a second part having the aspiration line component, the irrigation line component having a body with a bore extending therethrough and at least one small hole extending between the bore and the exterior, the at least one small hole being arranged to communicate, in use, with the fluid communication lumen, the aspiration line component including an annular collar arranged to receive the body of the irrigation line component, the fluid communication lumen extending from the annular collar to a tubular member of the aspiration line component, the irrigation line component being provided with at least two of the small holes spaced apart from one another, and means being provided for moving the irrigation line component to different positions in the annular collar to achieve different flow rates through the fluid communication lumen.

2. An aspiration flow modulation device according to claim 1, wherein the irrigation line component is arranged to be rotated by a tab to the different positions.

3. An aspiration flow modulation device arranged to be mounted in close proximity to a hand piece wherein the device comprises an irrigation line component and an aspiration line component, and wherein the irrigation line component is arranged to be mounted in close proximity to the hand piece and the aspiration line component is also arranged to be mounted in close proximity to the hand piece, and a fluid communication lumen is located between the irrigation line component and the aspiration line component so as to provide fluid communication between the components, the device being formed in a plurality of parts, a first part having the irrigation line component and a second part having the aspiration line component, one part having a body with a bore extending therethrough and at least one small hole extending between the bore and the exterior, the at least one small hole being arranged to communicate, in use, with the fluid communication lumen, the other part having an annular collar arranged to receive the body of the one part and a tubular member, and the fluid communication lumen extending from the annular collar to the tubular member of the one part, the one part being provided with at least two of the small holes spaced apart from one another, and means being provided for moving the one part to different positions in the annular collar to achieve different flow rates through the fluid communication lumen.

4. An aspiration flow modulation device according to claim 3, wherein the one part is arranged to be rotated by a tab to the different position.

* * * * *